(12) United States Patent
Ross

(10) Patent No.: US 6,434,423 B1
(45) Date of Patent: Aug. 13, 2002

(54) HIGH FREQUENCY ELECTRO MAGNETIC FIELD TREATMENT OF ABNORMALITIES

(76) Inventor: Jesse Ross, 321 E. Shore Rd., Great Neck, NY (US) 11023

( * ) Notice: Subject to any disclaimer, the term of this patent is extended or adjusted under 35 U.S.C. 154(b) by 0 days.

(21) Appl. No.: 09/566,954

(22) Filed: May 8, 2000

(51) Int. Cl.[7] .................................................. A61N 1/40
(52) U.S. Cl. ............................................ 607/2; 600/14
(58) Field of Search ........................ 600/13, 14; 607/2, 607/103, 135

(56) References Cited

U.S. PATENT DOCUMENTS 4,665,898 A * 5/1987 Costa et al. .................. 600/14
6,083,214 A * 7/2000 Ross et al. ..................... 600/2

FOREIGN PATENT DOCUMENTS

RU        1146066 A    *  3/1985   ..................... 607/2
RU        1344375 A    * 10/1987   .................... 600/13

* cited by examiner

Primary Examiner—William E. Kamm
(74) Attorney, Agent, or Firm—Myron Amer, P.C.

(57) ABSTRACT

In connection with the treatment of cell-related abnormalities with therapies heretofore having unavoidable adverse side effects, using a known high frequency electromagnetic therapy used heretofore for blood-related abnormalities having no significant adverse side effects, with the unobvious result that as a substitute therapy for the cell-related abnormalities there are also no adverse side effects characteristic of the use thereof for blood-related abnormalities.

1 Claim, 3 Drawing Sheets

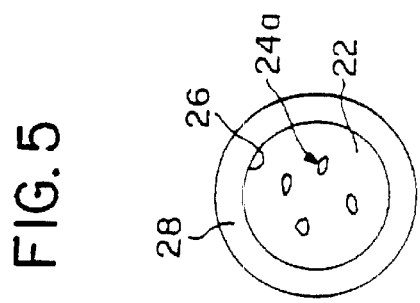
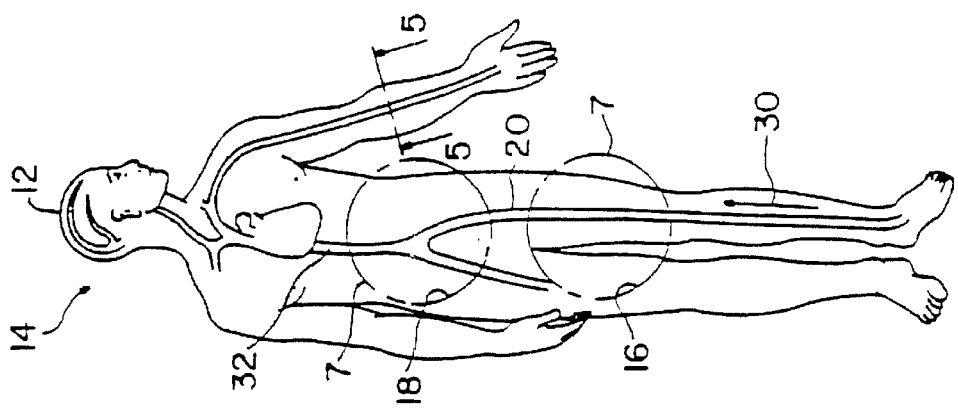
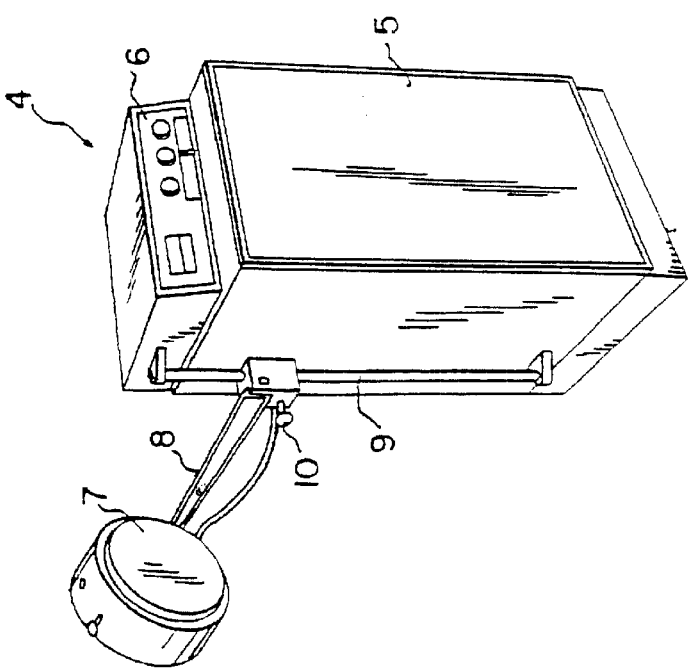

HIGH FREQUENCY ELECTRO MAGNETIC FIELD TREATMENT OF ABNORMALITIES

The present invention relates generally to improved effective treatment of two specified bodily abnormalities, one said bodily abnormality being blood-related and exemplified by a manifested migraine headache, and the other said bodily abnormality being cell-related and exemplified by uncontrolled cell profusion in a male prostate wherein the commonality in the treatments is exposure to a high frequency electromagnetic field and the resulting improvement, more particularly, is minimizing adverse side effects of current treatments.

Example of the Prior Art

Medical literature abounds with disclosures of treatments for bodily abnormalities of blood-related or cell-related natures. It is known by common experience that such treatments have adverse side effects. For example, the debilitating effect on the body, hair loss, and the like of chemotherapy, x-ray, cobalt, and surgery, and combinations thereof, in an effort to avert or abate the terminal consequence of cancer.

Another example is the treatment of migraine headaches which, by choice, was pharmacological in nature, although not effective for all types of migraine headaches and inappropriate for patients having allergic reactions to the medication. This is addressed and another treatment option afforded to sufferers of migraine headaches in my U.S. Pat. No. 5,718,721 for "Method of Relieving Headache Pain" issued on Feb. 17, 1998.

In the treatment of cell-related abnormality, specifically cell-related uncontrolled cell profusion in a male prostate, the aforesaid treatments of choice have significant side effects, and currently there is no option to use a treatment at least as, and believed to be more, effective than said chemotherapy, x-ray, cobalt, and surgery, and with no significant adverse side effects.

Broadly, it is an object to provide an optional treatment of bodily abnormalities overcoming the foregoing and other shortcomings of the prior art.

More particularly, it is an object, without significant side-effects, to provide a treatment of an identified cell-related prostate abnormality which contributes to an abatement of uncontrolled cell division, a known cause of terminal prostate cancer.

The description of the invention which follows, together with the accompanying drawings should not be construed as limiting the invention to the example shown and described, because those skilled in the art to which this invention appertains will be able to devise other forms thereof within the ambit of the appended claims.

FIG. 1 is a perspective view of an apparatus for generating an electromagnetic field for practicing the within inventive method;

FIG. 4 is a graphic of blood circulation;

FIG. 5 is a sectional view of the brachial artery as talken along line 5—5 of FIG. 4;

Figure 2:
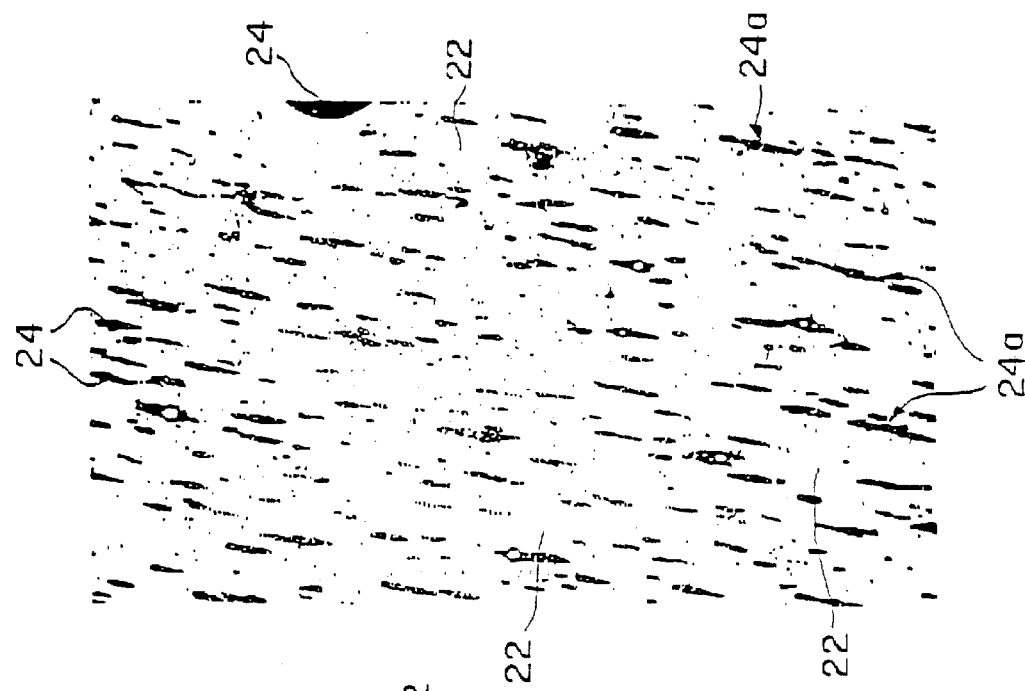
FIG. 2 is an illustration of a microphotograph of blood prior to the subjection to high frequency oscillation.

The Treatment Of A Migraine Headache Of U.S. Pat. No. 5,718,721

Shown in FIG. 1 is an athermapeutic apparatus for the generation of pulsed high frequency oscillations to which a patient is subjected of a type which is now well known to the art wherein the pulse frequency and duration is of such nature that the total time period during which electrical energy is actually induced into the body of a patient is so short that despite the comparatively high instantaneous energy level of the pulsed power it is unaccompanied by heat generation because the time for heat dissipation is many times longer than the heat accumulation. The athermapeutic apparatus is commercially available from Diapulse Corporation of America, located at 321 East Shore Road, Great Neck, N.Y. and, in the trade its mechanism of action is known as Diapulse Therapy.

Still referring to FIG. 1, the athennapeutic apparatus 4 as therein shown comprises a cabinet 5 provided with a control panel 6, for regulating the pulse repetition rate and pulse duration, timer setting, etc., and having a treatment head 7. Such treatment head is carried by an arm 8 to which it is pivotally connected, and with the arm in turn being reciprocally and axially movable on a tubular support 9 and secured in any desired adjusted position relative to the support 9 by a locking screw 10.

Apparatus 4 will be understood to generate an electromagnetic field having a pulse duration and frequency which is fixed at sixty five micro-seconds and for pulse frequencies of from eighty to six hundred pulses per second, so that even at its maximum setting the total peak energy of nine hundred seventy five watts maximum is of such short duration the average power is only twenty-five to forty watts. Accordingly, at the maximum pulse rate of six hundred pulses per second the rest period between the pulses is approximately twenty-four times as great as the duration of each pulse, so that any heat that might be accumulated in the patient during the occurrence of the pulse has many times longer for its dissipation, thereby providing a treatment which is not harmful to the patient.

Underlying the present invention is the recognition that the generated electromagnetic field of apparatus 4 can be used to advantage to relieve migraine headache patient-experienced pain, an end use not heretofore known, without adverse side effects. More particularly, it is generally believed that the headache of migraine is due to an abnormal diminished blood flow out of the patient's brain, e.g., the parietal lobe, as noted at 12, and the advantageous use herein made of the generated electromagnetic field generated by the apparatus 4 is to increase blood flow or circulation of a pain-relieving amount to the patient's brain, without any increase in the patient's heartbeat or any dilution of the patient's blood as might adversely impact on the health of the patient.

To the above end, to a patient 14 the head 7 of apparatus 4 is positioned in electromagnetic field penetrating relation to a selected body location of the patient remote from the patient's brain 12. The basis of selection of the body location is to make accessible to the generated magnetic field a main artery of the patient's circulatory system. Preferred-locations that have provided good results in practice is location 16 which will be understood to be the interior portion of the thigh, i.e., femoral area, and location 18 which will be understood to be the descending colon, both locations 16 and 18 being on or adjacent to the anterior tibial 20.

Figure 3:
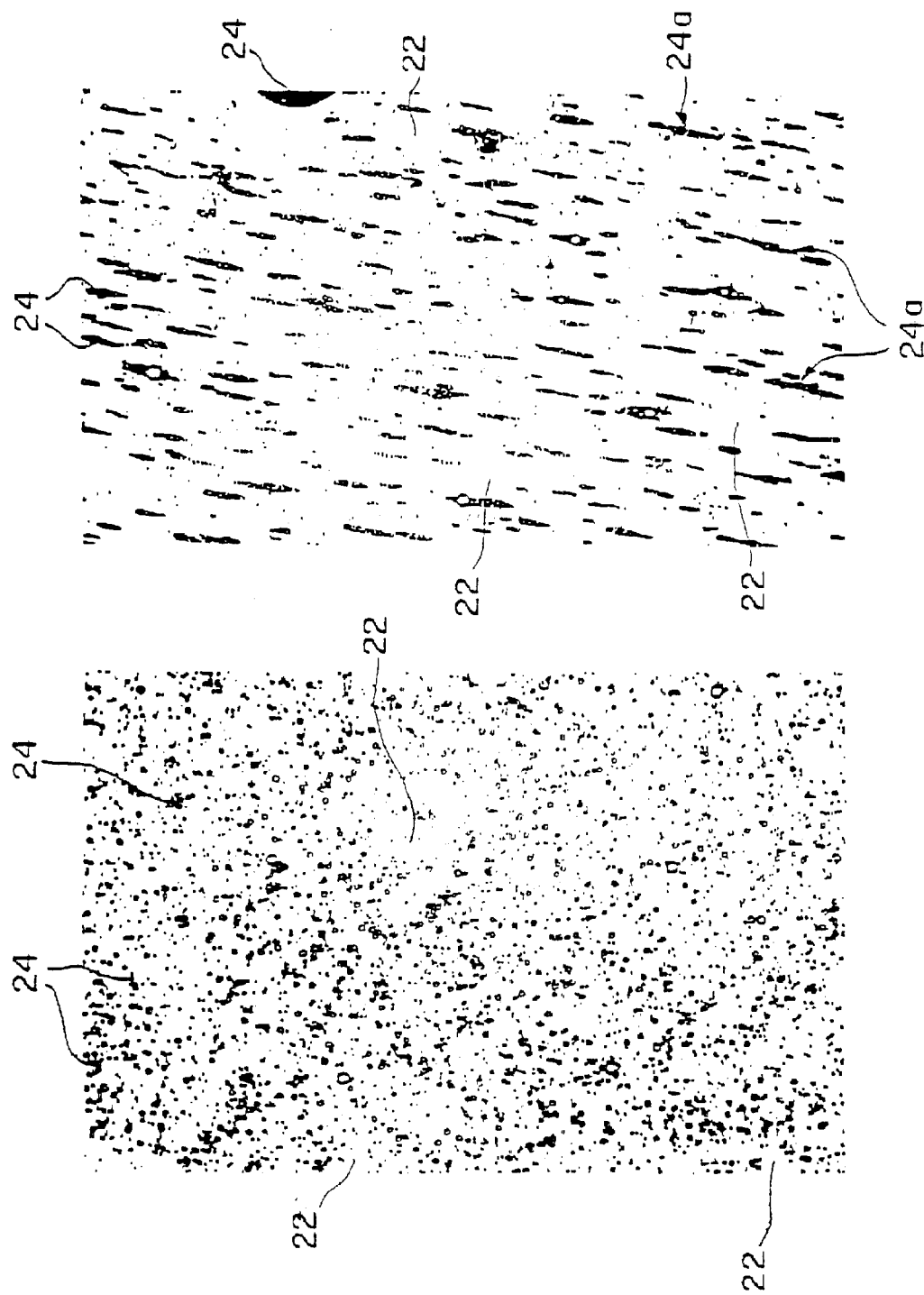
FIG. 3 is another microphotograph illustration of the blood of FIG. 2, but after subjection to the high frequency oscillation and showing a pearl chain formation of the nutritive blood elements.

The result of the impingement of the electromagnetic field on the blood is best understood from FIGS. 2 and 3, to which reference should now be made. Blank or unoccupied areas, individually and collectively designated 22 will be understood to be the fluid content of the blood, and the occupied areas, also individually and collectively designated 24, will be understood to be the nutritive elements of which the blood is composed, such as lymph, chyle, plasma, etc.

By comparison of FIG. 2 before subjection to the electromagnetic field, to FIG. 3 after subjection, it should be readily observable that the pattern of FIG. 2 is a random dispersion of the blood fluid and nutritive elements contents 22, 24, and that in FIG. 3 the nutritive elements 24 have assumed a chain-like formation, more particularly designed 24A, which formulation is known in the parlance of the art as a "pearl chain" formulation.

A physical noteworthy attribute provided by the pearl chain formulation 24A is its longitudinal orientation which, during blood flow in the longitudinal direction of the anterior tibial 20, by way of example, is flow with minimum resistance at the interface 26 of the blood 22, 24 and the interior cell wall or cell membrane 28, which is manifested as an increase in blood flow or velocity.

More particularly, at rest the velocity, designated 30, is 5.000 ml per minute, and when in a testing run the epigastrium, or abdominal aorta 32, was exposed to a penetrating electromagnetic field, the rate of blood velocity 30 was measured to increase 1.75 times the testing pulse, which increased from the base rate of 100. it was noted that the increase occurs during treatment and is maintained 1 to 8 hours.

In practice under the circumstances described, the patient 14 felt relief from the headache of migraine without attendant abnormal increase in heartbeat or any dilution of the blood, as might adversely impact on the health of the patient.

The Diapulse Theragy

In the treatment use of the apparatus 4, the electromagnetic field utilized might typically have the following specific parameters:

1. A frequency of 27.12 megahertz (11 meter band);
2. A pulse repetition rate of 80 to 600 pulses per second;
3. A pulse width of 65 microseconds;
4. A power range, per pulse, of between 293 and 975 watts;
5. A duty cycle between ½ of 1% to 3.9%; and
6. A square pulse, with a rise and fall time less than 1%.

The Treatment Of Uncontrolled Cell Division In The Prostate

Figure 7:
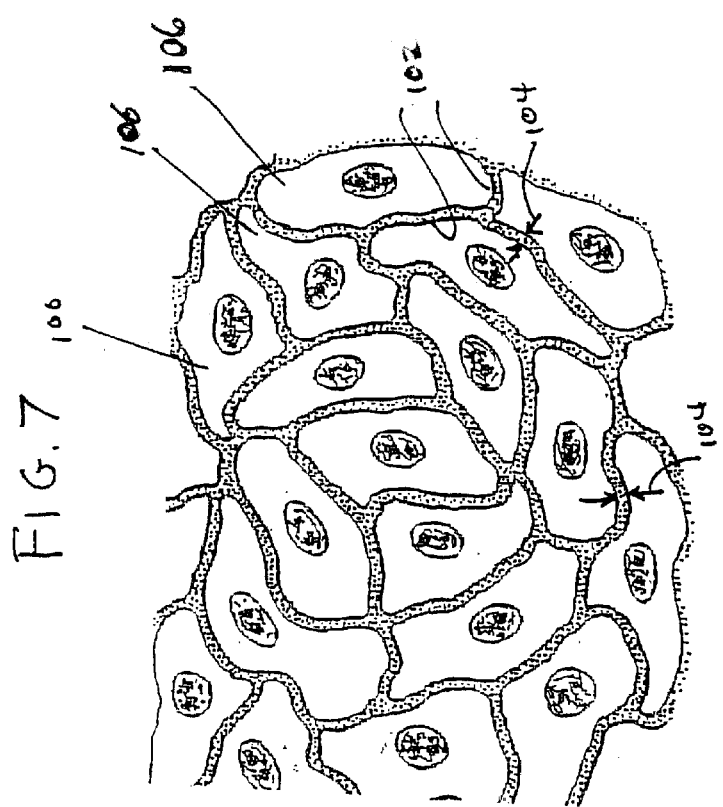
FIG. 7 is similar to FIG. 6, but depicting human cells in a life-supporting or healthy condition.

Depicted in FIG. 7 are "normal cells", individually and collectively designated 100, which by observation under great magnification supplemented by experimentation, are each known to be characterized by cell surfaces 102 at the interface 104 of which there is a strong bond maintaining the cells 100 immobile, the strong bond being provided by an Em (electromagnetic) high level, and consequently a division rate which is very low.

Figure 6:
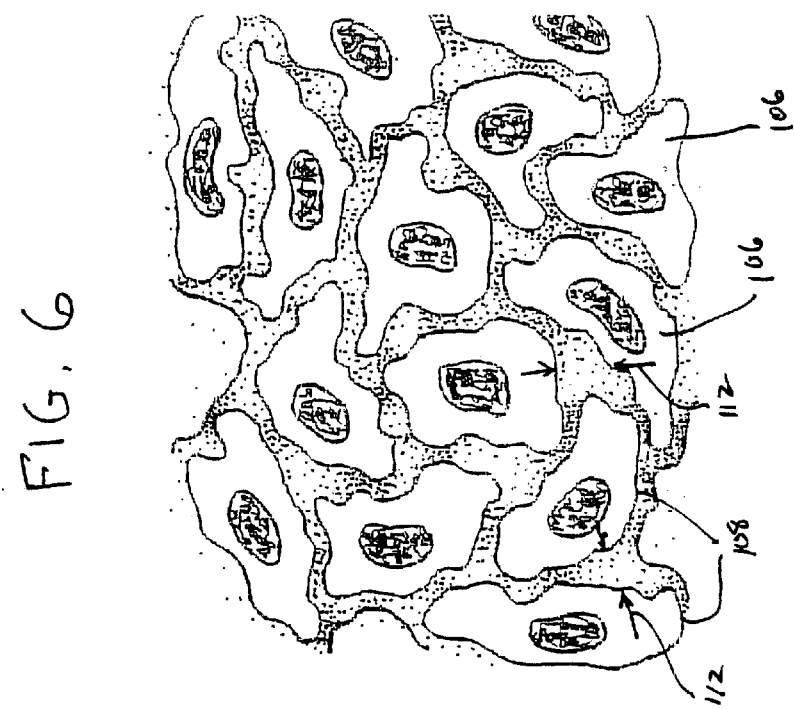
FIG. 6 depicts, on a greatly enlarged scale, human cells in a life-threatening or abnormal condition.

Depicted in FIG. 6 are "malignant cells", individually and collectively designated 106, which for reasons not filly understood but believed to result from malignant transformation by physical, chemical and viral carcinogens have altered, at cell surfaces 108, polymers. Under observation under great magnification supplemented by experimentation, measurement and the like, it has been determined that the bonding of the surface interfaces 110 is very weak, that the cells 106 are mobile and, as will be better understood as the description proceeds, the cells 106 invade normal tissue and cells 100 resulting in metastasizing wherein the Em level of each cell 106 is decreased and division of the cells 106, depicted as at 112, proceeds unchecked.

For many years the medical profession has used chemotherapy, x-ray, cobalt, and surgery, with very little progress in their fight against cancer. It is believed that if they would adjunctively utilize Diapulse Therapy, which has no reported contraindications, they may find that it could supply the missing element that they have been seeidng for the control of cancer.

An inactive cancer cell, i.e., cell 106, whose electrical potential may be twice that of a normal cell 100, attracts a positively charged protein, thus starving surrounding tissue. Once this stress, or any other stress occurs, the normal cells 100 are depolarized. This change in polarity causes the slowing down of the DNA and the RNA synthesis, as well as the sodium pump. In the process of repolorization, sodium and water accumulate in the cells 100, and potassium which normally travels freely through the cell membrane 102, is prevented from so doing. Edema that develops in the cell 100 creates a piezo-electrical effect due to the pressure against the adjacent cancer cell 106. Because sodium and water are excellent electrical conductors, and the cell 100 is seeking to restore its normal potential, negative ions are drawn from the cancerous tissue. Since the cancer cell 106 has no means of restoring its electrical potential, as it is outside the system, the drop of the electrical charge reaches a point of less than −10 mV, causing them to go into mitosis. This increased growth of the tumor continues until it reaches healthy tissue where it is contained. Unless the high electrical potential is maintained on the cancer cell 106, the above described process will be repeated until the patient dies.

By applying between 2 to 20 gauss of pulsed electromagnetic energy to the cancerous tissue and normal tissue, it is theorized it would be possible to prevent the lowering of the electrical potential of the cancer cell 106, and also eliminate or reduce the inflammatory process which occurs in normal cells 100. It is felt that if this can be maintained for a period of three or four months, the cancer cells 106 will self destruct or be placed in a dormant state.

The exposure of normal and cancer cells 100, 106 to less than 20 gauss will increase the electrical charge on the cancer cells 106. This occurs because it is not part of the system and cannot ground off any excess electrical charge, as do normal cells 100. If the Diapulse Therapy provider induces more than 20 gauss he would increase the electrical potential on normal cells 100 and thus create a stress, The inflammatory process which would occur would lower the potential on the cancer cell 106 and begin mitosis.

Diapulse Therapy is able to re-charge these normal cells 100 to their maximum levels and a process called the "electret theory", the reserve above the normal charge on healthy cells 100–usually 5%. In other words, if there is a −90 millivolt charge on cells, it might be increased to −95 millivolts. Any additional charge that the normal cells 100 are exposed to is discharged through the natural grounding mechanism of the body.

The electrical charge on the cancer cells 106 , when exposed to this energy, increases to a point where the nucleii of each cell becomes static in its function and therefore loses control over the estrogen sacs, at which point the estrogen destroys the nucleii of the cancer cells.

While the method herein shown and disclosed in detail is fully capable of attaining the objects and providing the advantages herein before stated, it is to be understood that it is merely illustrative of the presently preferred embodiment of the invention and that no limitations are intended to the detail of construction or design herein shown other than as defined in the appended claims.

What is claimed is:

1. A method of treating a patient's identified cell-dividing abnormality in adjacent relation to cell-nondividing normality exemplified by an occurrence in the prostate comprising the steps of:

A. recording by a first measurement an electrical potential of a cell of said cell-dividing abnormality;

B. impinging said cells of said cell-dividing abnormality and cells of said cell-nondividing normality with generated electromagnetic radiation of selected parameters;

C. selecting as said parameter one from a range of 80 to 600 pulses per second with a pulse width of 65 microseconds;

D. maintaining the aforesaid impingement at intervals of selected duration over a period of at least three months and not more than four months as determined by a second measurement of an electrical potential of cells of said cell-dividing abnormally indicating said electrical potential of said second measurement is at the level of, or above, the electrical potential of said recorded first measurement thereof; and E. exposing said cells of said cell-dividing abnormality during each impingement to generated electromagnetic radiation of less than 20 gauss to contribute to increasing an electrical charge on said cells of said cell-dividing abnormality and obviating exposure of said cells of said cell-nondividing normality during each impingement to generated electromagnetic radiation of more than 20 gauss as might contribute to increasing an electrical charge on said cells of said cell-nondividing normality, whereby an inflammatory process does not occur as would lower the electrical potential of the abnormality and begin mitosis of the cells thereof.

* * * * *